United States Patent [19]

Morle

[11] 4,263,256
[45] Apr. 21, 1981

[54] CUVETTES FOR AUTOMATIC CHEMICAL APPARATUS

[75] Inventor: Charles W. Morle, Gerrards Cross, England

[73] Assignee: Coulter Electronics, Inc., Hialeah, Fla.

[21] Appl. No.: 91,188

[22] Filed: Nov. 5, 1979

[51] Int. Cl.³ .................. G01N 35/02; G01N 21/03; G01N 21/13

[52] U.S. Cl. ........................ 422/66; 422/61; 422/102; 356/246

[58] Field of Search .................. 422/61, 66, 102; 356/246

[56] References Cited

U.S. PATENT DOCUMENTS

| | | | |
|---|---|---|---|
| 3,346,464 | 10/1967 | Ernst | 422/61 |
| 3,477,822 | 11/1969 | Hamilton | 422/61 |
| 3,497,320 | 2/1970 | Blackburn et al. | 422/61 |
| 3,545,934 | 12/1970 | Dryden et al. | 422/61 |
| 3,620,678 | 11/1971 | Guigan et al. | 422/66 |

Primary Examiner—Ronald Serwin
Attorney, Agent, or Firm—Silverman, Cass & Singer, Ltd.

[57] ABSTRACT

The invention relates to cuvettes for use in apparatus for the examination of liquid samples, such as automatic chemistry apparatus. Cuvettes are formed as a continuous integral strip, the strip between adjacent cuvettes being made flexible so as to permit relative angular movement of adjacent cuvettes in the horizontal and preferably both the horizontal and vertical planes in use. An apparatus for use with the cuvettes includes a carrier for receiving the cuvette strip in located position, and scanning means for scanning the cuvettes sequentially with appropriate radiation which is transmitted through the samples in the cuvettes.

9 Claims, 7 Drawing Figures

CUVETTES FOR AUTOMATIC CHEMICAL APPARATUS

This invention relates to cuvettes for use in apparatus for carrying out chemical reactions automatically.

In one method of chemical examination of samples, each sample is placed in a small container or cuvette, which is made of transparent material. A quantity of reagent is added to the sample and the progress of the resulting chemical reaction is monitored optically through the transparent walls of the cuvette. The monitoring can be carried out by a technician, using suitable optical apparatus, but where, as is often the case, there are many samples to be examined, it is more expeditious and economic to use an automatic apparatus in which a number of cuvettes containing samples are mounted on a suitable carrier, such as a turntable, and whilst on the carrier are examined by optical means which scans the samples in turn.

The chemical reactions which are monitored in this way are of two types: in the first of these examination is for the purpose of establishing when an endpoint condition has been attained, for example in chemical titrations when an endpoint is indicated by a change of colour of the indicator employed. Similar endpoint examination is made with certain tests carried out on blood serum. In the second type of examination, which can be identified as kinetic examination, the rate of progress of the reaction has to be examined, and in apparatus for this type of examination repeated optical examinations of each sample have to be made, at sufficiently short intervals of time for significant changes to be perceived, and over a period of time long enough for all significant changes to be seen.

The present invention is primarily concerned with a construction of cuvette which simplifies the loading of the cuvettes on to the carrier in an automatic chemical apparatus.

THE PRIOR ART

The present practice with regard to the cuvettes which are used in this type of apparatus is to mould the individual cuvettes from a suitable plastic material. The cuvettes have to be moulded to a high degree of precision, since the optical properties of the walls of the cuvettes and the material of which they are made are important. In use, the cuvettes are loaded individually on to the turntable or other carrier and after a cycle of movement are either removed and replaced each by a further cuvette, or the cuvettes are emptied, washed and cleaned ready to receive a further sample.

Proposals have also been made to make containers for use in a fraction collecting apparatus in such a way as to permit individual containers to be joined by interengaging means provided on the containers, thereby permitting a series of connected containers to be moved in an arcuate path in the horizontal plane.

THE INVENTION

The present invention is concerned with a construction of cuvette which simplifies the loading of the cuvettes on to the carrier, and which also permits simplification of the design of the examination apparatus itself. By the invention this is achieved by the provision of cuvettes in the form of a continuous integral strip, the individual cuvettes of the strip being relatively rigid, but the strip of cuvettes is so formed as to present a degree of flexibility in the plane of the strip, and preferably also in the plane at right angles thereto.

By making the cuvettes in the form of a continuous strip the loading of the cuvettes on to the carrier is much simplified, as compared with the handling of individual cuvettes; by making the strip of cuvettes flexible in the plane of the strip, which in use will be the horizontal plane, it is possible to feed the continuous strip about the periphery of, or about a circular path on, a rotating carrier, so that the cuvettes are then moved in a circular path convenient for scanning by rotary scanning means. By making the cuvettes in a continuous strip form they can be made in a continuous process from inexpensive plastic material, to the extent that it becomes economic to make the cuvettes disposable; this in turn simplifies the problem of removing the cuvettes after examination of the samples which they contain has been completed.

A further advantage accrues from making the strip of cuvettes in a manner which affords flexibility in both the vertical and horizontal planes. The reason for this is that in a suitable form of scanning apparatus for scanning the cuvettes in position on the carrier the light or other scanning radiation is projected horizontally, or approximately so, thriugh the cuvettes. To this end, one or more rotating elements direct the radiation through the cuvettes and a further optical element or elements used to receive the radiation after transmission through the cuvettes. Most conveniently such an arrangement calls for elements rotating one within and one without the circular path of the cuvettes on the carrier. By making the strip of cuvettes flexible in both planes, the introduction of the strip of cuvettes into the path defined by the carrier, between inner and outer elements of the scanning means, is facilitated.

In the operation of an apparatus with a continuous strip of cuvettes the loading of the cuvettes on the carrier can take place continuously, and it is not necessary for the carrier to be moved intermittently, as is usual with a conventional carrier loaded with individual cuvettes, though intermittent movement is possible if such movement is desirable for other reasons. When the examination of the samples has been completed, the cuvette strip can be disengaged from the carrier, and if disposable can be passed directly to waste.

THE DRAWINGS

Features and other advantages of the invention will be apparent from the following description of a preferred embodiment, in conjunction with the accompanying drawings, in which.

THE EMBODIMENTS OF THE INVENTION

Figure 1:
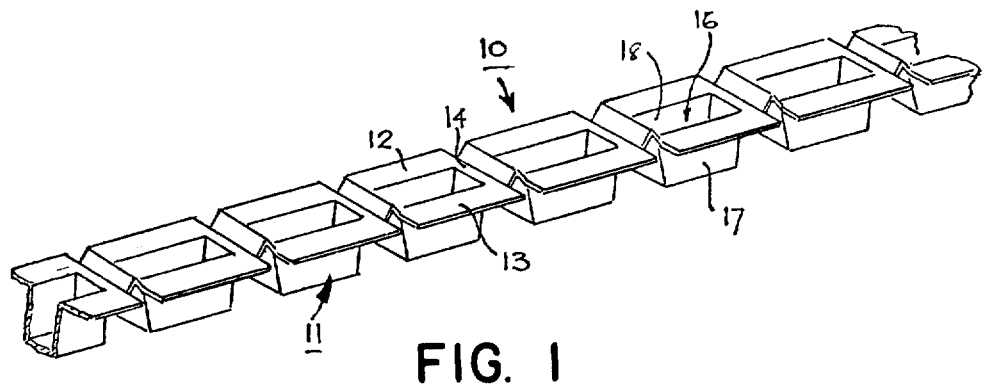
FIG. 1 is a partly diagrammatic perspective view of a short length of cuvette strip.
Figure 2:
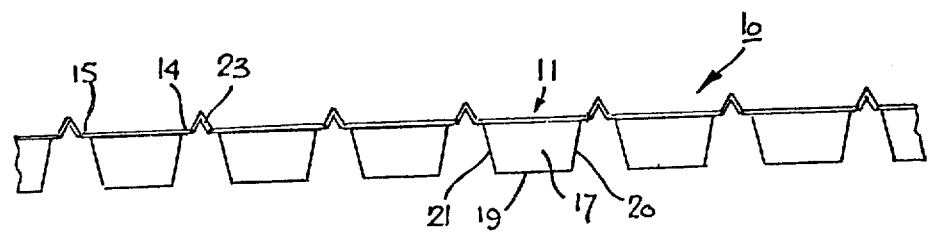
FIG. 2 is an elevational view of a length of the strip of FIG. 1.
Figure 3:
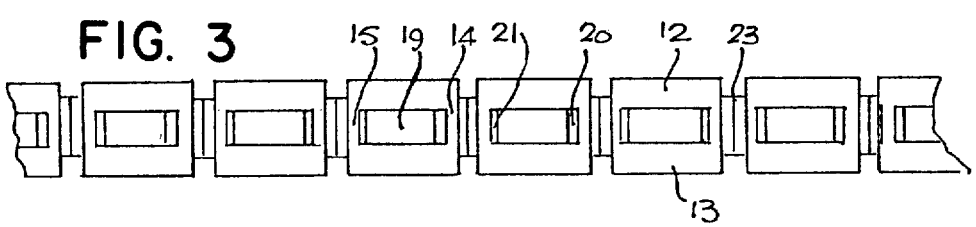
FIG. 3 is a plan view of the strip of FIG. 1.

FIGS. 1, 2 and 3 show a form of cuvette strip 10 which is intended for use in an automatic examination apparatus. The strip is composed of a thin transparent plastic material shaped to present a succession of similar cuvette sections 11. Each cuvette section has a generally flat upper surface with two edge portions 12 and 13, a forward portion 14 and a rearward portion 15; for a reason which will appear it is convenient if the four portions all lie in the same plane.

There is a central depressed receptacle portion 16, which is adapted to receive the sample under examination; this depressed part is defined in part by two opposed side walls 17 and 18 which are flat and parallel, and are spaced by a predetermined distance. As shown, the receptacle is completed by a bottom wall 19, and forward and rearward end walls 20 and 21.

The individual cuvette sections thus formed are relatively stiff, but each section is joined to the next by a neck portion 23, which is made flexible by being formed as or with one or more corrugations. This corrugated neck portion affords to the cuvette strip as a whole flexibility in the horizontal plane, that is, in the plane of the surface containing portions 12 to 15, and also in the vertical plane at right angles thereto.

The cuvette strip can be formed by heat-forming a strip of thermoplastic material; by this means the cuvette strip can be made in long lengths, permitting continuous feed to the examination machine. The shape of the cuvette sections, and especially the receptacle depressions, can be varied in shape, dimensions and proportions, as circumstances may dictate, but the construction adopted, in conjunction with the shape and proportions of the neck portions, should afford the desired flexibility, and the receptacle depressions should have opposite walls, such as walls 17 and 18, which are flat, parallel and accurately spaced if, as is intended, the cuvette strip is for use in an optical examination apparatus, for it is through these walls that radiation is transmitted for examination to be made.

For this reason the walls such as 17 and 18 should be finished accurately, approaching optical accuracy, but this degree of finish is not necessary for the rest of the cuvette strip. Accordingly, the cuvette strip can be first formed by a simple forming process, such as vacuum forming of heated thermoplastic strip, and punching out the unwanted parts of the strip, and then forming the walls such as 17 and 18 between dies, by which they can be given the desired accuracy of thickness, flatness and spacing.

Figure 4:
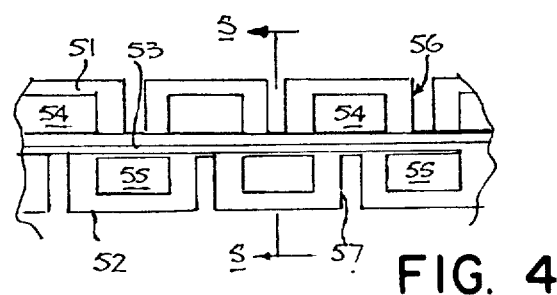
FIG. 4 is a plan view of an alternative form of cuvette strip.
Figure 5:
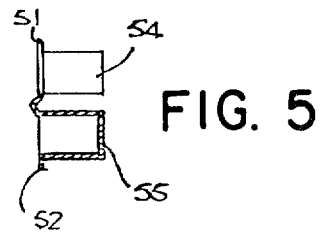
FIG. 5 is a sectional view of the cuvette strip of FIG. 4, taken on the line 5—5 of FIG. 4.

Other shapes and dispositions of the cuvette receptacles can be used, and one alternative is shown in FIGS. 4 and 5, to which reference is made hereafter.

Figure 6:
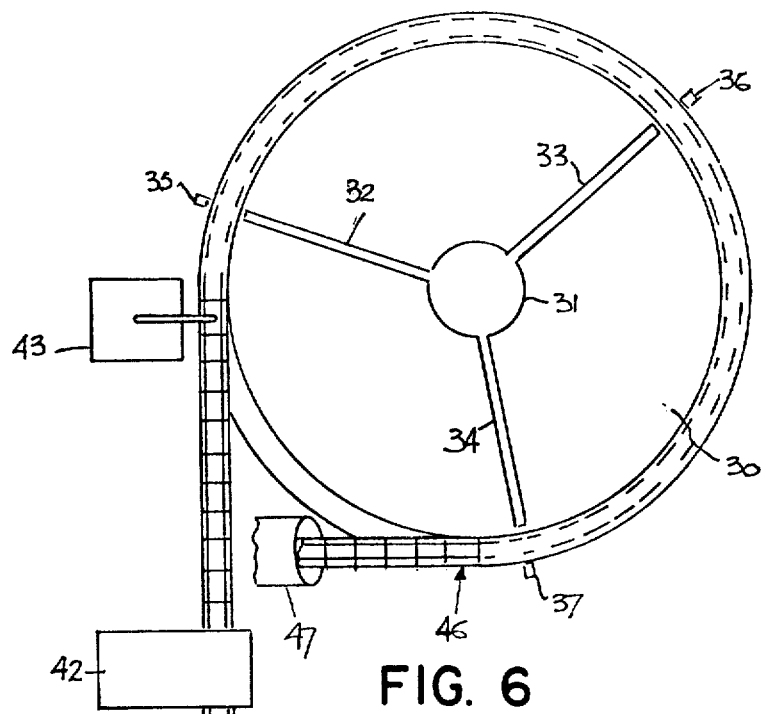
FIG. 6 is a diagrammatic plan view of an automatic examination apparatus.

An apparatus for the automatic examination of samples is shown diagrammatically in FIG. 6. It comprises a carrier 30 about the periphery of which, or on a defined circular path on which, is engaged the cuvette strip 10, the cuvette receptacles of which contain samples under examination. The carrier is rotated; the speed of rotation depends upon the type of examination being carried out, and in the case of kinetic measurement describe above the time taken for one revolution is at least as long as the samples in the cuvettes are to remain under examination. Examination is carried out optically, and for this purpose a light source, such as an electric lamp, not shown, is mounted in a central column of the carrier at 31, and light from the source is directed by suitable optical means into one or more paths towards the periphery of the carrier. As shown, light is directed into three paths within guides 32, 33 and 34; the guides can be in the form of optical systems including collimating and focussing elements within a tube, or use can be made of fibre optic elements. In some cases it is necessary or desirable to make examination with light of different wavelengths, and in this case each tube or guide can be dedicated to measurement at one of the wavelengths.

Light is directed from the guides or tubes on to the inner one of the side walls of the cuvette receptacles, and after being transmitted through the material of the sample the emergent light, the the intensity of which at the specific light wavelength is indicative of a characteriastic of the material of the sample, is received by a corresponding light collector 35, 36 or 37 and returned to a light sensitive element such as a photomultiplier; the resultant electric signals are then passed to signal processing circuits. For examination at different wavelengths there can be a separate light sensitive element for each relevant wavelength, or by suitable disposition of the light guides with respect to the cuvette positions it can be arranged that the responses from the three light systems are non-coincideent in time; the light from the three light systems can then fall in turn on the same light sensitive element and the different signals obtained by gating out the three signal sets. Any suitable arrangement of light elements and systems can be adopted, and one example of a possible arrangement is shown in Great Britain Pat. No. 1,501,883.

The cuvette strip is fed to the periphery of the carrier. The cuvette strip is taken from a supply reel 38 mounted for rotation on a shaft 39, and passed into guides 40 and 41 which engage the edge portions 12 and 13 of the cuvette sections. The guided strip 10 passes through a loading station 42, where samples of material to be examined are loaded into the receptacles of the cuvette sections. The strip, now bearing the samples, is passed to a station at 43 where the strip comes into contact with the periphery of the carrier, and at which position a measured quantity of reagent is added to the sample charged in each cuvette receptacle. In order that the exterior parts 35, 36 and 37 of the optical systems do not foul the cuvette sections as they pass into engagement with the carrier, the guides 40 and 41 which terminate at the reagent charging station 42 are bent downwardly in advance of station 42, this downward bending of the guides being permissable by virtue of the strip of cuvettes being flexible in the vertical plane.

Figure 7:
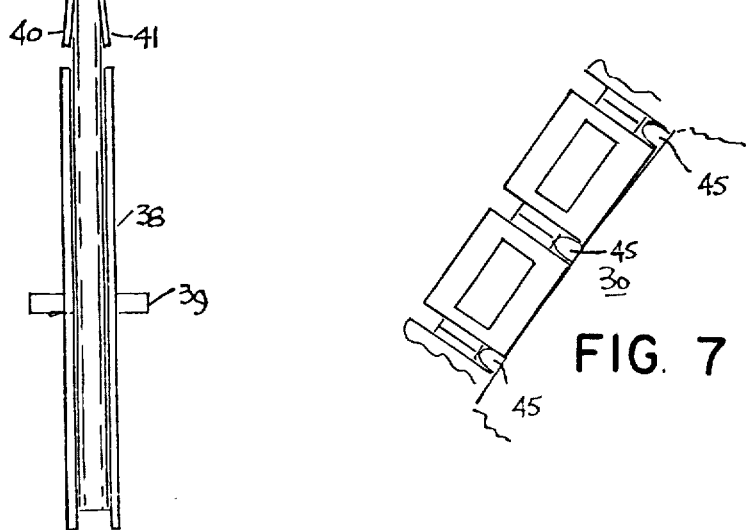
FIG. 7 is a fragmentary plan view of a detail of the carrier of FIG. 6, showing one method of locating the cuvettes on the carrier.

It is important that the cuvette sections should be accurately located and indexed on the carrier, and FIG. 7 is a detail showing a simple means to this end. The carrier is shown as being provided with a series accurately spaced projections 45, and as the strip passes into engagement with the carrier the projections enter the spaces formed by the neck portions of the strip. These projections also ensure that the strip moves with the carrier without slip, and the predetermined location of each cuvette section permits its identity to be preserved. Since there will always be a fixed number of cuvette sections between the loading station and a given cuvette position, the results from a particular sample can be extracted from the output signals.

At the completion of examination each cuvette will have progressed around the axis of the carrier until it is adjacent an unloading station at 46; at this station the cuvette strip leaves contact with the carrier and is lifted clear of the exterior parts of the optical systems and passes directly to a discharge chute 47. By using a disposable strip the complication of emptying and washing individual cuvettes is avoided.

The strip of cuvettes can engage the periphery of the carrier in a continuous feeding movement, and it is not necessary to operate the carrier in a step by step motion as has been the practice with prior apparatus. This restraint upon design is removed, and whether intermittent or continuous motion of the carrier is adopted depends more on the manner in which the sample and the reagent are introduced into the cuvette receptacles. It is often necessary to examine samples over a period of up to 30 or 40 minutes, and this means that the carrier will make one revolution in a period of this order of minutes. With a carrier of convenient diameter, such as 20 inches or 50 cms. the linear speed of the strip will be approximately 1 mm. per second, and at this low linear speed the reagent can be charged into each cuvette receptacle without stopping the carrier. However, the carrier can be moved intermittently, in known manner, and scanning of the cuvettes by the light system carried out while the carrier is stationary.

In kinetic examination by means of an apparatus of the type described the rate at which the carrier can rotate is dictated by the minimum time of examination of samples, and so depends upon the number of cuvettes which can be accommodated on the carrier. It follows that it is desirable to have on the carrier as many cuvettes as possible. The strip according to the invention can be modified to allow more cuvettes in a given length of strip, and in FIGS. 4 and 5 is shown a strip which has this advantage. This strip presents two rows of cuvette receptacles the individual receptacles of which are staggered. The strip 50 has edge portions 51 and 52 and a central corrugated portion 53. One series of receptacles 54 is arranged between the central corrugation 53 and edge portion 51, while the other series 55 is disposed between the central corrugation and the other edge portion 52. The receptacles are separated by slots 56 extending inwardly from edge portion 51, and receptacles are separated by slots along edge 52. Depending upon the material of which the strip is made, the corrugated central portion can be made more flexible by providing perforations in it at intervals. The staggered arrangement of the receptacles allows them to be separately scanned by the light system thus avoiding ambiguity of response.

With either of the configurations of strip described it is possible to apply to the outer surface of one of the side walls such as 17 or 18 a reflective coating, as by vacuum deposition or other application of a metal coating, such as aluminium, and the one side wall can also be shaped with a microstructure so-called corner reflector pattern; by such means radiation transmitted through one side wall is reflected back from the reflective surface of the other.

From time to time, when the apparatus described is used for examination of blood serum it may be desired to introduce a sample for emergency examination. In this case it is advantageous to arrange that the loading station 42 is located as close as possible to the reagent charging station 43, and to provide a "Load Omit" control, upon operation of which one or more receptacles are left unloaded with samples; the emergency sample or samples can then be loaded manually or by a supplementary loading mechanism, a suitable signal being transmitted to the signal circuits to indicate the revised order of samples.

The flexibility of the cuvette strip allows the strip to be moved in other then the simple circular path described while the samples are being examined. Linear or circularly arcuate paths are most convenient for scanning, but combinations of linear and arcuate paths can be used, and a plurality of strips following different paths can be accommodated on a single carrier. Multiple carriers, accommodating the same or different strips can also be used.

What is claimed is:

1. An integral cuvette strip for use in an apparatus for the examination of liquid samples, said strip comprising a series of connected cuvettes each presenting at least one open receptacle for a liquid sample, each said cuvette including a plurality of walls defining the respective receptacle thereof, two opposed walls of the said walls being optically transparent, each said cuvette being connected to an adjacent cuvette by a flexible integral portion of the strip permitting relative angular movement of said adjacent cuvettes both in a horizontal and a vertical plane with respect to said strip in use.

2. An integral cuvette strip as claimed in claim 1 wherein the two said walls of each cuvette are plane and parallel and of optical quality superior to that of other portions of the cuvette.

3. An integral cuvette strip as claimed in claim 1 wherein adjacent cuvettes are joined by a flexible integral portion of said strip which is corrugated whereby to provide said flexibility.

4. An integral cuvette strip as claimed in claim 1 wherein said cuvettes are positioned on said strip in staggered arrangement longitudinally of said strip.

5. An integral cuvette strip as claimed in claim 1 wherein said cuvettes are positioned on said strip with said receptacles of said cuvettes arranged in staggered nonoverlapping disposition longitudinally of the strip.

6. An integral cuvette strip as claimed in claim 1 wherein said strip is an integral strip of transparent plastic moulded to present said cuvettes and the flexible portions between them and thereafter further formed to shape the said opposed walls.

7. An apparatus for the examination of liquid samples, comprising a movable cuvette strip carrier, a cuvette strip located on said carrier for movement therewith, said cuvette strip comprising a series of connected cuvettes each presenting at least one open receptacle for a liquid sample, each said cuvette including a plurality of walls defining the respective receptacle thereof, two opposed walls of the said walls defing each receptacle being optically transparent, each said cuvette being connected to an adjacent cuvette by an integral flexible portion of said strip permitting angular relative movement of the said adjacent cuvettes both in a horizontal and a vertical plane, said apparatus further including a radiation source, radiation directing means for directing radiation from said source to and through cuvettes of said strip sequentially, and radiation receiving means for receiving radiation from said source passing through said cuvettes.

8. An integral cuvette strip as claimed in claim 1, wherein said flexible integral portions provide said strip with sufficient flexibility to enable said strip to be disposed in a substantially circular configuration in said horizontal plane with respect to said strip in use.

9. An apparatus as claimed in claim 7, wherein said flexible integral portions provide said strip with sufficient flexibility to enable said strip to be disposed on said carrier in a substantially circular configuration in said horizontal plane with respect to said strip.

* * * * *